United States Patent [19]

Patterson

[11] Patent Number: 4,473,495

[45] Date of Patent: Sep. 25, 1984

[54] ALBUMIN-SOLUBILIZED HYMENOPTERA VENOMS FOR VACCINE USE

[75] Inventor: Roy Patterson, Wilmette, Ill.

[73] Assignee: Northwestern University, Evanston, Ill.

[21] Appl. No.: 518,044

[22] Filed: Jul. 28, 1983

[51] Int. Cl.$^3$ .......................... A23J 7/00; C07G 7/00; C09H 00/00; A61K 39/36; A61K 39/00

[52] U.S. Cl. .................................. 260/112 R; 424/91; 424/88

[58] Field of Search ............... 260/112 R; 424/88, 85, 424/91, 78, 98

[56] References Cited

U.S. PATENT DOCUMENTS

| | | |
|---|---|---|
| 3,794,630 | 2/1974 | Mullan et al. |
| 3,809,782 | 5/1974 | Spector ............................. 260/121 |
| 3,983,229 | 9/1976 | Relyveld ............................. 424/92 |
| 4,009,267 | 2/1977 | Huber et al. ......................... 424/177 |
| 4,180,562 | 12/1979 | Patterson et al. ..................... 424/91 |

OTHER PUBLICATIONS

Patterson et al., J. Allergy. Clin. Immunol., 66: 495–499, (1980).
Patterson et al., J. Immunol., 110: 1413–1417, (1973).
Patterson et al., J. Allergy. Clin. Immunol., 59: 314–319, (1977).
Avrameas et al., Immunochemistry, (1969)., vol. 6, 53–66.
Boehm et al., Abstract 17, Abstracts of Scientific Papers, American Congress of Allergy and Immunology, Mar. 23–31, 1977, New York, NY.
Mueller et al., Abstract 126, Abstracts of Papers, 36th Annual Meeting of the American Academy of Allergy, Feb. 18–20, 1980, Atlanta, GA.

*Primary Examiner*—Lionel M. Shapiro
*Assistant Examiner*—Robin Teskin

[57] ABSTRACT

Hymenoptera venoms for vaccine immunization of human subjects are prepared by copolymerizing the venom with albumin using glutaraldehyde as the polymerizing reagent. Sufficient albumin is used to produce water-soluble copolymers of high molecular weight. The resulting water-soluble copolymers of molecular weights above 200,000 daltons are separated from the residual reagents, insolubles, and lower molecular weight polymers or copolymers.

4 Claims, No Drawings

ALBUMIN-SOLUBILIZED HYMENOPTERA VENOMS FOR VACCINE USE

GRANT SUPPORT

This invention was made in part under a grant from the National Institutes of Health, Grant No. AI 11403.

BACKGROUND AND PRIOR ART

The field of this invention relates to vaccines for hymenoptera stings, or more broadly to allergy vaccines for use in immunotherapy by subcutaneous injection.

Allergic reactions to hymenoptera stings are a serious problem. It has been estimated that nearly 1% of the general population in the United States has a hymenoptera allergy. Each year in the United States, nearly twice as many people die as a result of bites by hymenopteroud insects (including bees, wasps, hornets, and fire ants) than from poisonous snake bites. A majority of systemic reactions and deaths are due to allergic reactions to the venoms of these insects.

Hymenopteran venoms contains histamine, various kinins, and other vasoactive substances, phospholipases, and hyaluronidase. These substances are hemolytic and neurotoxic in addition to being effective hypersensitizing agents. In hypersensitive individuals, a single sting may produce serious anaphylaxis with urticaria, nausea, abdominal cramps, asthma, massive edema of the face and glottis, dyspnea, cyanosis, hypotension, coma, and death. Sensitization is usually the result of previous stings.

Hymenoptera venom preparations are available for clinical use in immunizing sensitive patients. Those approved for use by the Federal Food and Drug Administration include the freeze-dried venom of honey bees (*Apis melifera*), yellow jacket venom (*Vespula sp.*), yellow hornet venom (*Dolichovespula arenaria*), white-faced hornet venom (*Dolichovespula maculata*), and wasp venom (*Polistes sp.*). These venom preparations contain the allergenic protein of the hymenoptera venom in water-soluble form, and are dissolved in a suitable aqueous vehicle for subcutaneous administration.

Fire ants are another stingy insect of the order of hymemoptera. Allergic reactions are commonly experienced after fire ant stings. For diagnostic purposes, extracts of the whole bodies of fire ants have been used as well as the fire ant venom. The antigens responsible for the allergic reaction appear to be present in both preparations. Heretofore, immunotherapy has employed whole body fire ant extracts.

Clinically, immunization with the available hymenoptera venom preparations described above can be painful and protracted, and the injections must be given with extreme care to avoid adverse effects. To guard against anaphylaxis with sensitized patients, the initial injections must be given at a very low level, and injections must be administered at frequent intervals with progressively increasing dose levels. For example, the initial injection may contain 0.05 micrograms or less of venom protein, and after a series of up to fifteen injections, the dose level may reach 100 micrograms. A single hymenoptera sting, such as a bee sting, corresponds on the average to about 100 micrograms of venom protein. Therefore, it can be seen that the present practice of immunization begins the injections at much less than the level corresponding to one sting, such as 1/20 of a sting, while the maintenance immunization level of about 1 sting may be reached after a long series of injections.

It would be desirable to provide hymenoptera venom vaccines which can be administered at higher dose levels without undue risks to sensitive patients, thereby making it possible to reduce the number of doses required for immunization. Further, if the immunizing doses can be carried to a higher level so that a more complete immunization is obtained, subsequent maintenance injections can be given at longer intervals, and the maintenance injections can also be at higher dose levels increasing their immunizing effectiveness. It is known that immunizing vaccines of reduced allergenicity can be prepared from pollens by reacting the allergen with glutaraldehyde. Patterson et al, J. Immunol., 110: 1413–1417 (1973); Patterson et al, *J. Allergy Clin. Immunol.*, 59: 314–319 (1977). It is also known that proteins may be reacted with glutaraldehyde to form either water-soluble or water-insoluble polymers. See *Immunochemistry* (1969), Vol. 6, 53–66, Avrameas et al. U.S. Pat. No. 3,794,630 discloses pollens polymerized with glutaraldehyde in a substantially water-insoluble form.

Heretofore, very little has been published on polymerized or chemically modified hymenoptera venoms. Boehm et al reported in 1977 that they obtained an insoluble product by reacting formaldehyde with bee venom, but that they were able to obtain a soluble product by reacting glutaraldehyde with bee venom. The water-soluble glutaraldehyde polymer of bee venom was found to have antigenic activity and reduced toxicity. Boehm et al, Abstract 17, *Abstracts of Scientific Papers, American Congress of Allergy and Immunology*, Mar. 23–31, 1977, New York, NY. Subsequently, the same research group has reported that chemically modified bee venom in water-soluble form was prepared in three different ways: (1) polymerization with formaldehyde, (2) acetoacetylation, and (3) coupling to polyethylene glycol. Mueller et al, Abstract 126, *Abstracts of Papers, 36th Annular Meeting of The American Acedemy of Allergy*, Feb. 18–20, 1980, Atlanta, Ga.

Patterson et al attempted to prepare a soluble polymer of bee venom by glutaraldehyde treatment, as had been done with ragweed antigen E, and grass and tree pollen allergens. However, multiple experiments using variations in concentration of glutaraldehyde, reaction time, and temperature produced either no polymerization or the formation of a solid polymer product. *J. Allergy. Clin. Immunol.*, 66: 495–499 (1980). A micronized form of the insoluble bee venom polymer was found to be antigenic in rabbits. Subsequently similar insoluble preparations were made from other hymenoptera venoms and human clinical trials were initiated. IgG response to the respective venoms used occurred in the sensitive patients without local or systemic allergic reactions, but the IgG response was of low magnitude and short duration. Patterson et al concluded that polymerized insoluble venoms were safe but had not demonstrated efficacy and terminated this approach. (Unpublished findings.) Many other approaches were then tried for preparation of glutaraldehyde polymers of hymenoptera venoms in soluble form but without success prior to the present invention.

SUMMARY OF INVENTION

This invention is based in part on the discovery that hymenoptera venom and human serum albumin can be formed into high molecular water-soluble copolymers by reaction with glutaraldehyde. Human serum albumin (HSA) is non-allergenic and safe for administration to human subjects. By using sufficient HSA in relation to the venom protein, water-soluble high molecular weight hymenoptera venom-albumin copolymers (HVAP) can be produced. Such copolymers retain antigenicity while providing reduced allergenicity, both locally and systemically. The high molecular weight copolymers can be readily separated and recovered.

DETAILED DESCRIPTION

Most of copolymer products of the present invention can be prepared from commercially available hymenoptera venoms. These are supplied in a freeze-dried water soluble form. Those presently available include the venoms of honey bee, yellow hornet (*Dolichovespula arenaria*), white faced hornet (*Dolichovespula maculata*), paper wasp (*Polistes sp.*), and yellow jacket (*Vespula sp.*). Preferably, the venoms are substantially free of extraneous non-venom substances reactive with glutaraldehyde. More specifically the venom extracts should not contain alanine or similar substance which can react with glutaraldehyde and thereby interfere with the desired polymerization of the venom. Further, the venom preparations should also be free of phenol, which has sometimes been used as a preservative for venom extracts.

The venoms referred to above are preferably used in a purified, water-soluble form. It is believed, however, that less purified forms of the hymenoptera allergens can also be used if the more purified forms are not available.

In general, the copolymerization reaction is carried out in an aqueous medium containing the hymenoptera venom, the human serum albumin (HSA), and the glutaraldehyde. Preferably, in preparing the copolymers in accordance with the present invention, the water-soluble venom is dissolved in water to form an aqueous solution. For example, a phosphate buffered saline solution can be used. This solution is preferably sterilized by filtration, and diluted with sterile water to the desired concentration for the reaction, such as from about 10 to 50 mg/ml. This concentration is not critical, since the desired reactions will occur at higher or lower concentrations than those indicated.

The HSA is also dissolved in the aqueous medium such as the buffered saline. The amount of HSA required to convert the venom protein to high molecular weight copolymers which are water-soluble will vary with the particular venom. In general, however, sufficient HSA should be employed to produce a relatively large yield of water-soluble copolymers of molecular weight above 200,000 daltons. Based on present information, several times as much HSA protein should be used as venom protein. The ratios of venom to HSA may be conveniently estimated by optical density (O.D.) at 280 nm. This is a standard method of determining protein in solution. See McDuffie et al, *J. Immunol.*, 1956, 77: 193. On a O.D. basis it presently appears desirable to use in excess of 3 parts of HSA per part of venom protein. For example with respect to purified water-soluble bee venom, it appears that the preferred range is from 4 to 6 parts of HSA per part of purified venom protein (O.D. basis).

The amount of HSA required to form soluble polymers from substantially all of the venom protein can be determined by progressively increasing the ratio of HSA to venom protein until little or no precipitate is formed during the copolymerization. By using such ratios of HSA to venom protein, a large proportion of the protein allergens can be converted to glutaraldehyde-venom protein albumin copolymers (HVAP) of molecular weights above 200,000 daltons.

The glutaraldehyde reactant is then added under sterile conditions. The glutaraldehyde should preferably be present in excess, such as at a concentration of from about 0.25 to 0.35 mg per mg of venom protein. Providing sufficient glutaraldehyde is present for the desired copolymerization, this concentration is not critical.

The reaction conditions such as temperature and reaction time may be the same as previously used for polymerizing ragweed antigen with glutaraldehyde. For example, the reaction may be carried out at a temperature of from 20° to 30° C., such as 25° C. Agitation of the reaction mixture is not required. After sufficient polymerization has occurred to form the high molecular weight water-soluble copolymers, further polymerization may be prevented and the reaction terminated by adding glycine or comparable reagent.

In an optimized reaction procedure, a high percentage, such as over 90%, of the purified water-soluble venom can be converted to water-soluble copolymers of high molecular weight. Some solid material may remain, or some precipitate may form which is either an insoluble polymer of the venom and glutaraldehyde or a non-water soluble copolymer of the HSA and the venom protein. Following completion of the reaction, therefore, the solution should be filtered to remove any solid materials. Thereafter, the high molecular weight copolymers are separated and recovered by a suitable procedure such as chromatographic separation. Other methods of separation may be used for commercial processing which are capable of making a relatively clean separation of the high molecular weight copolymers, such as copolymers above 200,000 daltons. Such methods include ultrafiltration using a membrane which permits the polymers, copolymers, and other solubles to pass through while retaining the high molecular weight polymers, such as those above 200,000 daltons.

Based on present information, it appears that the most desirable separation of the copolymers is at 240,000 daltons, thereby obtaining copolymer fractions in the range of 240,000 and above. The final product should be free of residual reactants, such as glutaraldehyde, or unreacted venom protein, or HSA, and the copolymer product should also be preferably substantially free of water-soluble copolymers and/or polymers, which have molecular weights below the specified cut-off.

The solution of the copolymers may be used to prepare vaccines for immunizing sensitive subjects against the particular hymenoptera venom. It may be necessary to adjust the concentration by adding a sterile injectable solution, or by removing part of the water by evaporation to produce a higher concentration. In general, desirable concentrations on a total protein basis will range from about 1 mg to 50 mg/ml.

Where the copolymers have been recovered in dry form, such as by vacuum evaporation of the water, copolymers may be redissolved in a suitable carrier. For example, the vehicle may comprise phosphate buffered to 0.15 molar NaCl containing 0.4% phenol. Other injectable vehicles can be used for administration of the copolymers which are adapted for subcutaneous injection. The copolymers may be packaged and distributed as concentrates, and diluted to the desired concentration for injection by addition of a suitable vehicle. This may be convenient, since in clinical use, progressively increased concentrations will be used in a series of injections for immunization of the subject.

The present invention is further illustrated by the following experimental examples.

EXAMPLE I

A high molecular weight mixture of honey bee venom and human serum albumin (BVAP) was prepared as follows:

Purified, water soluble honey bee venom (Sigma Chemical Co., St. Louis, Mo.) 5 mg, as estimated by optical density (O.D.) at 280 nm, and 27 mg (by O.D. at 280 nm) of chromatographically purified human serum albumin (Cappel Labs., Cochranville, Pa.) were dissolved in 0.15M phosphate buffered NaCl, pH 7.35 (PBS). The venom and albumin were polymerized at 0.008M glutaraldehyde (25% glutaraldehyde solution) supplied by Allergy Labs of Ohio, Columbus, Ohio. Total volume was 4.3 ml. Polymerization was carried out at room temperature for 3 hrs, and 95 mg of glycine was added to stop further polymerization. The solution was mixed for 20 min and centrifuged for 10 min at 1200 xg. The supernatant was chromatographed on a Sephacryl S-300 superfine (Pharmacia Fine Chemicals, Piscataway, N.J.) column previously calibrated with dextran blue 2000 (Pharmacia) and chromatographically pure human serum albumin (HSA). Those fractions which were eluted before the albumin peak were used as the polymer preparation, hereinafter referred to as "BVAP". These were combined and O.D. measured. The column was calibrated by determining the solution pattern of catalase prior to the chromatograhic experiments on BVAP.

EXAMPLE II

Using the copolymer product prepared as described in Example I, the following tests were conducted:

Immunization of rabbits with bee venom-albumin copolymer (BVAP)

BVAP was used to immunize rabbits with 7 weekly subcutaneous injections of 2.6 mg protein (estimated by O.D. at 280 nm). Blood samples for studies of the immune response were taken at 0 time and biweekly from then on for 14 weeks. Sera were obtained by centrifugation, and stored at −20° C.

Enzyme linked immunosorbent assay (ELISA) for measurement of antibody against bee venom A micro ELISA method was used. Volter et al, *Bull. World Health Organ.*, 53 & 55 (1976). Briefly, immulonmicroplates (Dynatech Labs., Alexandria, Va.) were used. The coating buffer was 0.1M Tris-0.15M NaCl pH 7.9. Other buffers were the same as described by Voller et al. The only other modifications were: (1) plates reacted coated with antibody dilutions were incubated for 1 hour at 37° C. and (2) alkaline phosphatase conjugated goat anti-rabbit IgG or rabbit anti human IgG were incubated for 1.5 hour at 37° C., instead of at the room temperature. Plates were read for an O.D. at 410 nm on a Microelisa minireader MR 590 made by Dynatech Instruments, Inc., (Santa Monica, Ca.)

Inhibition of human and rabbit anti bee venom by bee venom

A human antisera against bee venom was obtained from a private source. Rabbit antisera prepared as described above were used. These antisera were titered by the ELISA technique. The highest dilutions of antisera were selected which produced the greatest O.D. separation of positives from negative control sera. To these antisera dilutions and normal human or normal rabbit serum dilutions, increasing amounts of either bee venom, or BVAP were added. Volumes were kept constant by the addition of buffer. All antisera and control sera were incubated at 4° C. for 30 min and overnight at 4° C. with the inhibiting antigens. Varying dilutions of these mixtures were added to the ELISA wells precoated with bee venom or BVAP and the residual antibody activity was measured as described above.

Radioiodination of bee Phospholipase A (PL-A)

Bee phospholipase A was obtained from Sigma Chemical Company (St. Louis, Mo.) and labeled with $^{125}I$ utilizing the chloramine-T method of Gleich et al, *J. Lab. Clin. Med.*, 77: 690 (1971).

Incorporation of $^{125}I$ bee PL-A into BVAP

Approximately 0.2 ug of $^{125}I$ PLA was added to a mixture of 5 mg of bee venom and 27 mg of HSA and polymerization of this mixture was carried out in the manner described above. Each Sephacryl S-300 chromatographic fraction was checked for O.D. at 280 nm and total radioactivity and the appropriate fractions combined as in the preparation of BVAP. Protein bound counts were determined after 10% trichloacetic acid precipitation. From the data obtained the extent of incorporation of $^{125}I$ PL-A into the BVAP could be determined.

Measurement of antibody against bee phospholipase A in rabbit anti BVAP

For this assay, a modification of the ammonium sulfate technique of Lidd and Farr was used, as described by Patterson et al, *J. Allergy Clin. Immunol.*, 66: 495 (1980).

Results

The results of the test are summarized as follows:

Chromatographic profiles of dextran blue, bee venom, human serum albumin, catalase and bee venom-albumin polymer using Sephacryl S-300 (S 300)

Catalase and human serum albumin separated with close peaks. Untreated bee venom gave a wide profile. After polymerization of bee venom and human serum albumin, the polymers were in both the excluded and included fractions of S-300. Only the fractions with higher molecular weights than catalase (M.W. 240,000) are used for the bee venom albumin polymer (BVAP) preparation.

Immune response of rabbits immunized with BVAP

Rabbits were immunized with BVAP prepared from the S-300 chromatographic separation. Both rabbits demonstrated an immune response to bee venom as demonstrated by the ELISA technique. The antibody responses were of similar levels in both rabbits. The antibody levels declined after immunization was terminated.

Antibody activity of human anti bee venom sera against BVAP

Using the ELISA technique, wells were coated with BVAP. Three human sera were analyzed for antibody activity against BVAP. These sera were from a bee keeper sera pool (141 ug IgG antibody against phospholipase A) and two individual sera with antibody against bee venom. The results showed antibody activity in all 3 human sera against BVAP.

Inhibition analysis demonstrating antigenic completeness of BVAP

This study was done to determine if the antigens in bee venom albumin polymer would inhibit human antibody reactions against bee venom. These results show that preincubation with BVAP will almost completely inhibit the subsequent reaction of human antiserum with bee venom. Higher concentrations of BVAP as compared with bee venom are necessary to achieve similar degrees of inhibition.

Neutralization of antibody against BVAP by bee venom and human serum albumin

This study was done to determine if there was evidence of new antigenic determinants on BVAP as evidenced by failure to inhibit anti BVAP with bee venom and albumin. The titer of a rabbit anti BVAP was determined using ELISA with wells coated with BVAP. Simultaneously, the titer was determined after the anti BVAP had been preincubated with a mixture of 50 ug each of bee venom and human serum albumin. The titer of the neutralized anti-BVAP was reduced to 1:640 (2 times NRS control) from the unneutralized anti-BVAP titer of 1:10,240 (FIG. 4). If new antigenic determinants were present on BVAP as a result of the polymerization process, absorption of the anti-BVAP with bee venom plus albumin should not have reduced the titer to near control levels.

Incorporation of $^{125}I$ phospholipase A (PL-A) into BVAP $^{125}I$ PL-A was mixed with bee venom and human serum albumin. This mixture was polymerized and fractionated on S-300. Bee venom PL-A has a molecular weight of about 40,000 daltons. Over 96% of the radioactivity was associated with molecules of higher molecular weight than albumin demonstrating that polymerization of a majority of PL-A occurred. Since polymers larger than catalase are used for BVAP, 92% of the PL-A of monomer was incorporated into polymers with molecules weights in excess of 240,000.

Antibody responses to PL-A in rabbits immunized with BVAP

Peak antibody levels were reached at around 4 weeks. Thereafter, the antibody levels declined from peak levels during continued immunization injections. This decline was similar to that observed in rabbits with ragweed antigen E polymerized with glutaraldehyde, which has been proven an effective immunogen in humans.

EXAMPLE IV

Using the general reaction procedure of Example I, a series of tube samples were prepared containing varying ratios of human serum albumin (HSA) to purified bee venom (BV). The protein weight ratios were determined and compared by optical density measurements (O.D.) at 280 nm. As shown by the data summarized below in Table A, increasing the ratio of HSA to BV progressively decreases the amount of precipitate, and by using a sufficient amount of HSA, all of the BV may be maintained in solution as a copolymer.

TABLE A

| Tube Sample | Approximate Mg. HSA (O.D.)/ 5 mg. BV (O.D.)[1] | Precipitate Formed[2] | |
|---|---|---|---|
| | | Time | Quantity |
| 1 | 0.54 | 1 min. | heavy |
| 2 | 2.7 | 1 min. | heavy |
| 3 | 5.4 | 2 min. | heavy |
| 4 | 10.8 | 2 hrs. | moderate |
| 5 | 16.2 | 2 hrs. | moderate |
| 6 | 27 | 3 hrs. | none |

[1]Both HSA and BV were determined by optical density (O.D.) at 280 nm, 1 mg protein (HSA or BV) equaling 1 O.D. unit. (Weight amounts of HSA were nearly double O.D. values, viz. 1 mg. by weighing equalled 0.54 mg O.D.)
[2]Semi-quantitative visual observations are indicated. (It should be noted that HSA polymerized with glutaraldehyde does not produce a precipitate under the same conditions.)

I claim:

1. Polymerized hymenoptera venom for vaccine use, comprising the reaction product of a hymenoptera venom (HV), human serum albumin (HSA), and glutaraldehyde, said product being composed of copolymers of HV and HSA containing sufficient HSA in relation to HV to make said product water-soluble.

2. The product of claim 1 in which said HV is bee venom.

3. Copolymers of a hymenoptera venom and human serum albumin, said copolymers having been formed with glutaraldehyde as the polymerizing reagent, said copolymers being water-soluble and having molecular weights in excess of 200,000 daltons.

4. Copolymers of a purified water-soluble hymenoptera venom and human serum albumin, said copolymers having been formed with glutaraldehyde as the polymerizing reagent, said copolymers being water-soluble and having an average molecular weight in excess of 240,000 daltons, said copolymers being substantially free of glutaraldehyde and polymers or copolymers of said venom having molecular weights below 240,000 daltons.

* * * * *